United States Patent [19]

Galle

[11] Patent Number: 5,420,723
[45] Date of Patent: May 30, 1995

[54] ARRANGEMENT FOR TRANSMISSION AND RECEPTION OF ELECTRO-MAGNETIC RADIATION

[75] Inventor: Bo Galle, Göteborg, Sweden

[73] Assignee: Aktiebolaget Institutet for vattenoch luftvardsforskning Halsingegatan 43, Sweden

[21] Appl. No.: 674,378

[22] PCT Filed: Oct. 16, 1989

[86] PCT No.: PCT/SE89/00566
§ 371 Date: Jun. 3, 1991
§ 102(e) Date: Jun. 3, 1991

[87] PCT Pub. No.: WO90/04761
PCT Pub. Date: May 3, 1990

[30] Foreign Application Priority Data
Oct. 17, 1988 [SE] Sweden .................. 8803695

[51] Int. Cl.⁶ .................. G01J 3/42; G01N 21/31
[52] U.S. Cl. .................. 359/857; 359/900; 356/303; 356/436; 250/338.5; 250/574
[58] Field of Search .............. 359/850, 857, 858, 859, 359/861, 863, 864, 900; 356/318, 326, 436, 437, 438, 440, 303, 307, 434; 250/338.5, 574, 340, 341

[56] References Cited

U.S. PATENT DOCUMENTS

| | | |
|---|---|---|
| 3,215,842 | 11/1965 | Thomas .................. 359/529 |
| 3,984,685 | 10/1976 | Fletcher et al. .................. 250/338.5 |
| 4,496,839 | 1/1985 | Bernstein et al. .................. 250/338.5 |
| 4,632,563 | 12/1986 | Lord, III .................. 250/338.5 |

FOREIGN PATENT DOCUMENTS 0070726 5/1980 Japan .................. 250/338.5

*Primary Examiner*—Ricky D. Shafer
*Attorney, Agent, or Firm*—Lerner, David, Littenberg, Krumholtz & Mentlik

[57] ABSTRACT

Arrangement for transmission and reception of electromagnetic radiation. A transmitting and receiving part (1) transmits and receives the electromagnetic radiation, and a reflecting part (2) reflects the transmitted electromagnetic radiation back to the transmitting and receiving part while passing through a medium which transmits radiation. The transmitting and receiving part has an electromagnetic radiation source (5) and a concave main reflector (3) which is common to transmission and reception. The transmitting and receiving part has a second reflector (6), which is positioned between the radiation source (5) and the main reflector (3), so that this second reflector shades a part of the main reflector reflecting area (4) for the radiation transmitted by the radiation source towards the main reflector. This forms a shadow area (17) on the main reflector reflecting area for transmitted radiation. This second reflector receives a part of the reflected radiation from the main reflector and reflects this back towards a detector for reception of the radiation. The shadow area for transmitted radiation also has a reflecting receiving area for the radiation which is incident upon the main reflector and reflected back towards the detector by the second reflector. The remaining part of the main reflector reflecting area, which is not shadow area for transmitted radiation, forms a transmitting area for the radiation which is transmitted by the radiation source and reflected in the main reflector.

14 Claims, 1 Drawing Sheet

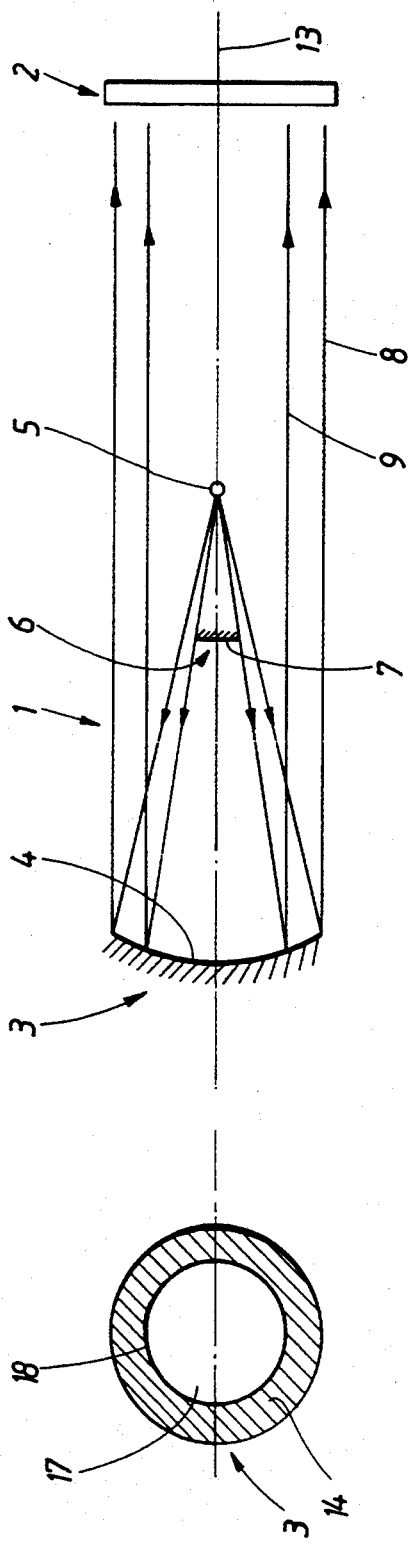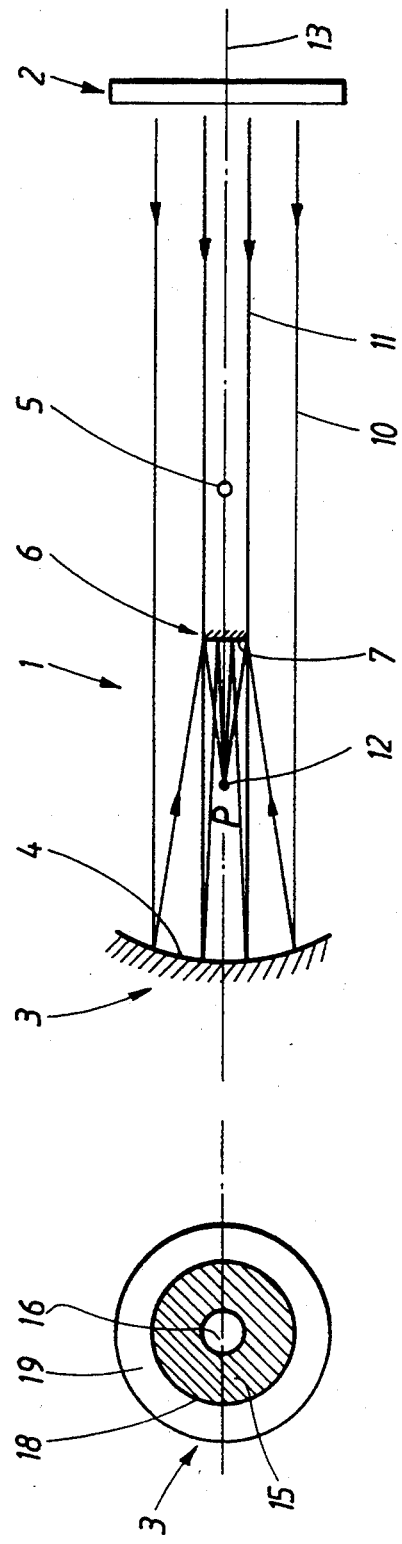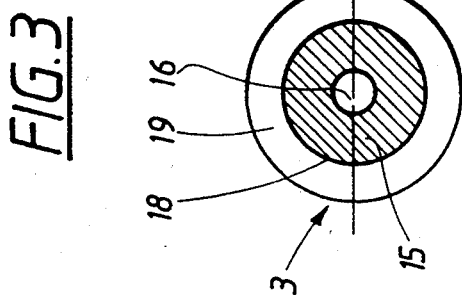

ARRANGEMENT FOR TRANSMISSION AND RECEPTION OF ELECTRO-MAGNETIC RADIATION

BACKGROUND OF THE INVENTION

The present invention relates to an arrangement for transmission and reception of electromagnetic radiation, consisting of a transmitting and receiving part for transmission and reception of the electromagnetic radiation, and a reflecting part, arranged so as to reflect the transmitted electromagnetic radiation back to the transmitting and receiving part, while passing through a medium which transmits radiation. The transmitting and receiving part includes an electromagnetic radiation source and a concave main reflector which is common to transmission and reception.

Transmission and reception of electromagnetic radiation is of interest in a number of applications, for example in measurement of air pollution, distance measurement etc. In this connection, use is made of visible or invisible light, for example, which is transmitted over a measuring distance, after which the light is collected and analyzed. In order to be able to transmit light over great distances without too great losses in intensity, use is made of telescopes. In this connection, a light source is positioned close to the focus of a parabolic or spherical mirror. After reflection in the mirror, light in the form of a parallel luminous beam is transmitted. After transmission through the atmosphere, a part of the luminous beam is collected with a receiving telescope constructed in similar manner and is focussed into a spectrometer, either by direct connection or via an optical fibre. In the case of direct connection, use is made, for example, of a so-called Newton arrangement with a mirror arranged at an angle in front of the receiving mirror.

An alternative to positioning transmitter and receiver at either end of the measuring distance is to transmit the radiation out and back over the measuring distance via a reflector. In this connection, all the components in the system must be accurately aligned, since transmitter and receiver are normally positioned next to one another, so that the radiation which is reflected back must be directed in a different direction from the transmitted radiation.

A suitable type of reflector for positioning at the far end of the measuring distance would be a so-called retroreflector, which is an optical component in which a number of reflecting areas are arranged in such a manner that the light which strikes the same is returned in the opposite direction, even in the case of incident light which deviates to a certain extent from the direction of the normal. By virtue of the fact that a retroreflector usually has a relatively high angular tolerance, the requirement for alignment and stability is relatively low. However, use of retroreflector in the known arrangement described above, with transmitter and receiver positioned side by side, would still occasion problems. The maximum intensity of the reflected light would in fact go back into the transmitting telescope and only a small part would reach the receiver.

SUMMARY OF THE INVENTION

The aim of the present invention is to bring about an arrangement for transmission and reception of electromagnetic radiation, in which transmitter and receiver are positioned in the same place and in which the arrangement is easy to align.

Said aim is achieved by means of an arrangement according to the present invention, which is characterized in that the transmitting and receiving part has a second reflector, which is positioned between the radiation source and the main reflector, so that this second reflector on the one hand shades a part of the main reflector reflecting area for the radiation transmitted by the radiation source towards the main reflector, forming a shadow area on the main reflector reflecting area for transmitted radiation, and on the other hand receives a part of the reflected radiation from the main reflector and reflects this back towards a detector for reception of the radiation, which shadow area for transmitted radiation also comprises a reflecting receiving area for the radiation which is incident upon the main reflector and reflected back towards the detector by the second reflector, the remaining part of the main reflector reflecting area, which is not shadow area for transmitted radiation, forming a transmitting area for transmitted radiation, forming a transmitting area for the radiation which is transmitted by the radiation source and reflected in the main reflector.

BRIEF DESCRIPTION OF THE DRAWINGS

The invention is described in greater detail below using an exemplary embodiment with reference to the attached drawings, in which FIG. 1 shows schematically an arrangement according to the invention with the ray path for transmitted radiation drawn in, FIG. 2 shows schematically an arrangement in which the ray path for the incident radiation is drawn in, FIG. 3 indicates the main reflector reflecting area which is used upon transmission of the radiation and FIG. 4 shows the main reflector reflecting area which is used upon reception of incident radiation.

DETAILED DESCRIPTION

The example shown envisages an arrangement for measuring air pollution, with which light is transmitted over a measuring distance of, for example, 100 m to 10 Km, after which the light is collected and analyzed by means of a spectrometer. In this connection, an absorption spectrum of a given gas is selected between a transmitter and a receiver, the spectrometer measuring the intensity of the received light as a function of the wavelength within a given wavelength band. According to the example shown, electromagnetic radiation of the light type is used, which can lie within the visible or invisible wavelength range. To this end, the arrangement according to the invention has a combined transmitting and receiving part 1 and a reflecting part 2, which consists of a separate unit situated at a distance from the transmitting and receiving part with, in between, the gaseous medium which is to analyzed. The transmitting and receiving part 1 is made up of a main reflector 3 in the form of a concave mirror, which is expediently designed with a parabolic or spherical mirror surface 4. A light source 5 in the form of a lamp is positioned on the optical axis 13 of the arrangement, close to the focus of the concave mirror 3. Between the light source 5 and the concave mirror 3, a second reflector 6 is positioned, which forms part of the transmitting and receiving part and the reflecting area 7 of which is turned towards the reflecting area 4 of the concave mirror 3. According to the example shown, this second reflector is designed as a plane mirror. Furthermore, both the concave mirror 3 and the plane mirror 6 are advantageously designed with circular shape, that is to say forming with their periphery a closed circular curve. This circular curve of the plane mirror has a radius of curvature which is less than the radius of curvature of the periphery of the concave mirror 3, that is to say the plane mirror 6 covers an area which is considerably smaller than the area of the concave mirror 3.

An example of the dimensional relationships, in the case of a distance to the reflecting part 2 of approximately 1 km, is as follows: the distance along the optical axis 13 between the radiation source 5 and the concave mirror 3=1.2 m, the distance between the two mirrors 3 and 6=0.9 m and thus the distance between the light source 5 and the plane mirror 6=0.3 m. The concave mirror 3 has a diameter with regard to its periphery of, for example, 0.3 m, whereas the plane mirror 6 should in this connection have a diameter of approximately 0.05 m.

The reflecting part 2 has a diameter of, for example, approximately 0.15 m and is advantageously circular accordingly. In principle, the reflecting part 2 can consist of a plane mirror but advantageously consists of a retroreflector, which reflects the incident light in the opposite direction parallel to the incident light within a given angular range for the angle of incidence. By these means, the exact alignment of the reflecting part 2 becomes non-critical.

In FIG. 1, for the sake of clarity, only the ray path in the case of transmission of the radiation and only the components which influence this are shown. In this connection, it has been indicated above that the light source 5 is positioned close to the focus, which in practice means that it is not necessarily positioned exactly at the focus, resulting in the rays reflected by the concave mirror 3 not being completely parallel, owing to the fact that the reflecting part is not positioned at infinite distance, for which reason the transmitted ray beam has rays 8, 9 which are slightly convergent. These deviations are, however, very small, for which reason it is possible to speak of the light source being positioned in the general area of the focus and of the transmitted rays from the concave mirror being essentially parallel.

FIG. 2 shows in a corresponding manner only the ray path for the rays 9, 11 which are reflected from the reflecting part 2 and incident upon the transmitting and receiving part 1. A collecting element for the ray beam, which is situated on the optical axis 13 at a point 12 between the concave mirror 3 and the plane mirror 6, belongs to the receiving components in the transmitting and receiving part. This collecting element can consist of a light guide for guiding the collected light to a spectrometer for spectral analysis of the received ray beam.

By means of the arrangement according to the invention described above, with the smaller mirror 6 positioned between the light source 5 and the larger, concave mirror 3 and turned towards the latter, and with a size of the smaller mirror which is selected in relation to on the one hand the positioning of the smaller mirror and on the other hand the size of the larger, concave mirror, it is brought about on the one hand that the smaller mirror shades the larger mirror from the rays which are transmitted from the light source and directed towards the larger mirror and on the other hand that, by means of the smaller mirror, only a part of the essentially parallel rays, which are incident upon the larger mirror and reflected back, is received. This is seen in both FIG. 1 and FIG. 2, and is clarified schematically in FIGS. 3 and 4, which show the different zones into which the surface of the concave mirror 3 can be divided by means of the effect of the smaller mirror 6.

The mirror surface 4 of the concave mirror can thus be divided into three zones, namely a first zone 14, which is annular in the example shown, constitutes a transmitting area and is hatched in FIG. 3, a second zone 15, which is likewise annular in the example shown, constitutes a receiving area and is hatched in FIG. 4, and a third, circular zone 16, which forms a shadow area for incident rays and is not used. The shape of these zones is determined by the shape and mutual positioning of the two mirrors 3, 6 and in the example shown the mirrors have a circular outer contour and are positioned symmetrically in relation to the optical axis 13. According to the invention, the receiving area 15 lies within an area which is at the same time a shadow area 17 for the radiation transmitted by the light source 5 towards the concave mirror 3.

Briefly, the arrangement according to the invention functions in the following manner, the transmitted radiation, which is shown in FIG. 1, being described first. A ray beam is transmitted from the light source 5, preferably in a direction which is essentially towards the concave mirror 3. The latter is struck by the ray beam in the first zone 14, that is to say the transmitting area, since a part of the mirror surface 4 is shaded by the smaller, plane mirror 6 in such a manner that the shadow area 17 for the transmitted ray beam is formed. By virtue of the fact that the light source 5 is situated in the area of the focus of the concave mirror 3, the annular ray beam is reflected in the concave mirror in essentially parallel rays, which are propagated through the gaseous medium which is to be analyzed. As a result of a diffraction, aberration, reproduction effects and, where appropriate, parallel shift in the reflecting part 2, the transmitted light beam with annular cross-section becomes "fused" and is returned, after reflection in the reflecting part 2, as a collected light beam. The ray path described, from the light source 5 and to the reflecting part 2 after passage through the gaseous medium, can thus be seen from FIG. 1. Parallel shift occurs in the reflecting part 2 in the event of use of a suitable reflector, such as one of the types of retroreflector available on the market. A suitable retroreflector is, for example, made by Precision Lapping Optical Co. U.S.A. By means of parallel shift in the reflecting part, the rays undergo, upon reflection, parallel shift through a distance which is determined by the construction of the reflector, which thus contributes to the fact that the transmitted annular ray beam becomes "fused". The extent of the parallel shift is adapted to the radial dimension of the receiving area 15 and the transmitting area 14.

The ray path after reflection in the reflecting part 2 is to be described now with reference to FIG. 2. The reflected ray beam 10, 11 accordingly passes back through the gaseous medium as essentially parallel rays and again strikes the mirror surface 4 of the concave mirror 3, with the exception of that part of the incident ray beam which strikes the plane mirror 6 and is thus obscured by the latter, as a result of which the shadow area 16 is formed for incident rays. However, not all the ray beam which is incident upon the concave mirror 3 and reflected by the latter strikes the plane mirror 6 on its mirror surface 7. This depends upon the relationship between the size of the two mirrors and the positioning of the smaller mirror 6 along the distance between the light source 5 and the concave mirror 3. By these means, the receiving area 15 is created, which thus falls within the shadow area 17 for the transmitted ray beam and thus forms a common circular boundary line 18 between shadow area 17 and the transmitting area 14 for transmitted rays and between the receiving area 15 for incident rays and surrounding area 19 of the mirror surface 4 of the concave mirror 3. The area 19 brings about reflection of the rays to the areas outside the outer contour of the plane mirror 6. The fact that the ray beam, which is incident upon the concave mirror 3 and reflected by the reflecting part 2, arrives to a large extent within the boundary line 18, that is to say within the receiving area 15, depends, as mentioned above, on the one hand on imperfections in the optical components and refraction phenomena in the transmission medium and on the other hand also, in the chosen example, on parallel shift in the reflecting part, by which means the light rays can be "shifted in" to the receiving area 15 with a selected parallel shift. The ray beam, which is incident upon the mirror surface 7 of the plane mirror 6, is reflected in the mirror surface 7 in such a manner that the ray beam converges towards the point 12, that is to say towards the collecting element, to be conveyed onward via, for example, the light guide or mirrors arranged at an angle towards a place outside the incident ray beam to a spectrometer for special analysis.

With the arrangement described above, transmitting and receiving part can thus be arranged in the same place without having to be positioned side by side, which leads to a number of advantages, such as:

only one component must stand in a stable manner and be aligned accurately;

all complicated components are in one and the same place;

only one place requires a power supply;

measurement over several distances can be made more economical;

the same light source as is used in measurement is also available for calibration for compensation of instrument factors;

the measuring distance can be halved while retaining sensitivity.

The invention is not limited to the exemplary embodiment described above and shown in the drawings, but can be modified within the scope of the following claims. It is not, for example, in itself necessary that the plane mirror 6 is positioned symmetrically on the optical axis 13, but it can even be positioned in such a manner that it only partially projects into and shades the ray beam. The same effect occurs in fact, irrespective of the laterally displaced position of the mirror in relation to the optical axis, namely that the receiving area 15 falls within the shadow area which occurs for the transmitted ray beam. The radiation source 5 also can be positioned outside the optical axis 13. Furthermore, it is not necessary that the mirrors are designed with a circular outer contour, but they can have another shape. The smaller mirror 6 does not necessarily need to be plane, but can also be concave or convex. Other types of telescope principle can be used, for example the Cassegrain type, in which case the point 12 is behind the concave mirror 3. In the latter case, an opening is arranged in the concave mirror for the passage of the rays which are reflected back from the smaller mirror.

In the example shown, an arrangement for measuring air pollution by means of spectral analysis is considered.

The construction and the functioning of the arrangements after the collection at point 12 can be of per se conventional type, for which reason these should require no more detailed description. Exactly the same arrangement, with the exception of the part which concerns the spectrometer, can be used for distance measurement, in which case the distance is quite simply determined starting from measurement of the time lag between transmitted ray beam and received ray beam, which is indicated, for example, in pulses, and with knowledge of the velocity of propagation of the radiation. Alternatively, the distance can be determined by means of measurements of phase shift of monochrome transmitted light. The arrangement can also be used for completely different purposes and can in this connection be used in conjunction with electromagnetic radiation of another type, for example, microwave radiation or radio waves. It is even conceivable that radiation within completely different wavelength ranges is possible, such as sound waves, for example ultrasound. The medium in between, through which the ray beam is transmitted, can also be a liquid or solid medium.

The collecting element 12 can be situated outside the light beam, which is incident upon the concave mirror 3, in which case the smaller mirror 6 is arranged at an angle of e.g. 45° for a 90° deflection of the ray beam, which is incident upon the smaller mirror, to the collecting element which in this connection can be constituted by the light input to the spectrometer.

The reflecting part 2 can also consist of a simple plane mirror. Use of a retroreflector with parallel shift is thus not a necessary prerequisite for the invention, but rather an advantageous embodiment.

In the claims, reference is made to the positioning of the detector. The collecting element, which can accordingly convey the collected light beam onwards to another place, is in this connection equated with the term detector.

As in the case in most optical systems, the ray path can be reversed, while retaining the basic function. In this connection, however, the light source 5 and the collecting element or the detector 12 must change places. The light source is thus positioned between the main reflector 3 and the second reflector, while the collecting element 12 or the detector is positioned beyond the reflector 7, at the focus of the main reflector in the example shown. The light source, in the example shown, is positioned in such a manner that the sum of the distance between the main reflector 3 and the second reflector 6 and between the latter and the light source is equal to the focal distance of the main reflector. Furthermore, the size and position of the reflector are selected in such a manner that the radiation transmitted by the light source, after reflection in the reflector 6, illuminates a part of the main reflector, but not all. The part of the main reflector illuminated in this manner constitutes a transmitting area, while the remaining part of the main reflector constitutes a receiving area for the radiation which returns from the retroreflector 2. The part of the returning radiation which falls within the receiving area is focussed to the collecting element 12. The reflector 6 also has the characteristic of shading the collecting element from direct or reflected (but not via the retroreflector) radiation from the light source.

I claim:

1. An apparatus for the transmission and reception of electromagnetic radiation comprising:

a.) a concave reflector having a first central focal axis and an outer defining edge with a first circular portion centered about said central focal axis for receiving electromagnetic radiation impressed thereon and a second circular portion centered about said central focal axis and extending from the outside edge of said first circular portion to the edge of said reflector for transmitting electromagnetic radiation impressed thereon;

b.) a first reflector having a second central focal axis, said second central focal axis of said first reflector corresponding with said first central focal axis of said concave reflector said first and second focal axes creating a common focal axis, said first reflector being spaced a first predetermined distance from said concave reflector along said common central focal axis, said first reflector reflecting transmitted electromagnetic radiation from said second circular portion of said concave reflector passing through a medium which permits the passage of electromagnetic radiation therethrough, back to said first circular portion of said concave reflector through said medium as reflected radiation;

c.) an electromagnetic radiation source positioned on said common focal axis of said concave and said first reflectors;

d.) a detector for receiving electromagnetic radiation reflected from said first circular portion of said concave reflector, said detector being positioned on said common focal axis between said concave reflector and said electromagnetic radiation source; and e.) a second reflector positioned between said electromagnetic radiation source and said concave reflector on said common focal axis to permit said second reflector to shield said first circular portion of said concave reflector when electromagnetic radiation is applied to said second circular portion of said concave reflector by said electromagnetic radiation source so as not to receive such electromagnetic radiation and to shield said second circular portion of said concave reflector when electromagnetic radiation is applied to said first circular portion of said concave reflector from electromagnetic radiation reflected from said first reflector, said second reflector reflects a portion of the reflected radiation from said first circular portion of said concave reflector to said detector.

2. An apparatus as defined in claim 1, wherein
a.) said concave reflector has a focal length and an area of focus and said second reflector is separated from said concave reflector along said common central focal axis by a first distance and said second reflector is spaced from said electromagnetic radiation source along said common central focal axis by a second distance, and the sum of said first and said second distances equals the focal length of said concave reflector resulting in a substantially parallel beam of electromagnetic radiation being transmitted from said second circular portion of said concave reflector;

b.) said first reflector receives said parallel beam of radiation and reflects said parallel beam of radiation in a substantially parallel form to said first circular portion of said concave reflector which in turn reflects said beam towards the area of focus of said concave reflector;

c.) said detector separated from said second reflector along said common focal axis by a third distance, the sum of said first distance and said third distance being equal to the focal length of said concave reflector.

3. An apparatus as defined in claim 2 wherein said second reflector is positioned along said common focal axis and is of a diameter, with relation to the diameter of the concave reflector, that said first and second circular portions of said concave reflector are of essentially the same size.

4. An apparatus for the transmission and reception of electromagnetic radiation comprising:
a.) an electromagnetic radiation source;
b.) a transmitting and receiving device for the transmission and reception of electromagnetic radiation initially emanating from said radiation source;
c.) said transmitting and receiving device comprising: a concave reflector having a first central focal axis, a focal point and an outer defining edge, with a first circular portion centered about said first central focal axis for transmitting electromagnetic radiation impressed thereon and a second circular portion centered about said first central focal axis and extending from the outside edge of said first circular portion to the edge of said reflector for receiving electromagnetic radiation impressed thereon;
d.) a first reflector arranged to reflect the transmitted electromagnetic radiation from said second circular portion of said concave reflector passing through a medium which permits the passage of electromagnetic radiation therethrough back to said first circular portion of said concave reflector through said medium as reflected radiation;
e.) a detector for detecting reflected radiation;
f.) a second reflector positioned along a second central focal axis common with said first central focal axis of said concave reflector, said first and second focal axes forming a common focal axis and positioned along said common focal axis at a position between the surface of said concave mirror and the focal point of said concave reflector;
g.) said second reflector having a reflecting surface facing the reflecting surface of said concave reflector;
h.) said radiation source being positioned along said common focal axis of said concave reflector and said second reflector;
i.) said second reflector being arranged to direct radiation from said radiation source to said first circular portion of said concave reflector while preventing such radiation from falling upon said second circular portion of said concave reflector or directly upon said detector from said radiation source; said first circular portion of said concave reflector arranged to transmit radiation towards said first reflector;
j.) said second circular portion of said concave reflector arranged to receive radiation reflected from said first reflector and reflects such radiation to said detector.

5. An apparatus according to claim 4, wherein said concave reflector has a focal length and an area of focus, and said second reflector is spaced from said concave reflector along their common focal axes by a first distance and said second reflector is spaced from said electromagnetic radiation source along their common focal axis by a second distance, the sum of said first and second distances being equivalent to the focal length of said concave reflector resulting in a substantially parallel beam of electromagnetic radiation being transmitted from said first circular portion of said concave reflector; said second circular portion of said concave reflector is arranged to reflect a beam of electromagnetic radiation impinging upon it in a substantially parallel beam in a direction towards said area of focus of said concave reflector; said second reflector spaced along said common focal axis from said concave reflector by a first distance and said detector is spaced from said second reflector by a third distance, the sum of said first and third distances being equal to the focal length of said concave reflector.

6. An apparatus as defined in claims 2 or 5 wherein said first reflector is retroreflective and reflects said reflected radiation from said first reflector substantially in parallel to said transmitted beam of radiation within a prescribed angular range corresponding to the angle of incidence of the transmitted beam of radiation upon said first reflector.

7. An apparatus as defined in claim 6 wherein said concave reflector and said second reflector each have an essentially circular configuration and that said second reflector is positioned along said common focal axis and separated from said electromagnetic radiation source by a distance approximately equal to ¼ of the distance between said source of electromagnetic radiation and said concave reflector.

8. An apparatus as defined in claims 1 or 4, wherein said radiation source comprises a light source and said concave reflector and said second reflector are each mirrors.

9. An apparatus as defined in claims 1 or 4 wherein said first reflector is arranged to effect a parallel shift of the beam of radiation upon reflection from said first reflector in an amount in dependence upon the radial dimension of said second circular portion of said concave reflector with respect to the radial dimension of said first circular portion of said concave reflector.

10. An apparatus according to claim 1 or 4 wherein said second reflector consists of a plane mirror positioned on said first focal axis of said concave reflector and with its plane face perpendicular to said focal axis of said concave reflector.

11. An apparatus as defined in claims 2 or 5, wherein said first circular portion of said concave reflector is arranged to reflect electromagnetic radiation impinging thereon with a parallel shift depending upon the radial dimension of said first circular portion of said concave reflector as compared to the radial dimension of said second circular portion of said concave reflector.

12. An apparatus as defined in claim 11, wherein said second reflector is positioned symmetrically on said first central focal axis of said concave reflector and has a diameter which is between 0.15 and 0.20 times the diameter of said concave reflector.

13. A method of employing the apparatus of claims 1 or 4, said method comprising positioning said apparatus in a medium through which electromagnetic radiation is passed, and analyzing the reflected radiation received by said detector to determine the composition of the medium through which said electromagnetic radiation was passed.

14. The method according to claim 13, in which said transmitted radiation is collected in said detector which forms part of a spectrometer for spectral analysis.

* * * * *

UNITED STATES PATENT AND TRADEMARK OFFICE
CERTIFICATE OF CORRECTION

PATENT NO. : 5,420,723
DATED : May 30, 1995
INVENTOR(S) : Galle

It is certified that error appears in the above-indentified patent and that said Letters Patent is hereby corrected as shown below:

On the Title Page, in the listing of attorneys, "Krumholtz" should read --Krumholz--.

Column 2, line 44, "Km" should read --km--.

Signed and Sealed this

Thirty-first Day of October 1995

Attest:

BRUCE LEHMAN

Attesting Officer

Commissioner of Patents and Trademarks